United States Patent [19]

Bacha et al.

[11] 4,138,412

[45] Feb. 6, 1979

[54] SIMULTANEOUS PRODUCTION AND PURIFICATION OF 4-NITRO-OMICRON-PHTHALIC ANHYDRIDE

[75] Inventors: John D. Bacha; Charles M. Selwitz, both of Monroeville, Pa.

[73] Assignee: Gulf Research & Development Company, Pittsburgh, Pa.

[21] Appl. No.: 814,212

[22] Filed: Jul. 11, 1977

[51] Int. Cl.$^2$ .......................................... C07D 307/89
[52] U.S. Cl. .............................. 260/346.3; 260/346.4; 260/346.7
[58] Field of Search ............... 260/346.3, 346.4, 346.7

[56] References Cited

U.S. PATENT DOCUMENTS

| | | | |
|---|---|---|---|
| 3,357,994 | 12/1967 | Popp et al. | 260/346.7 X |
| 3,720,692 | 3/1973 | List et al. | 260/346.7 |

*Primary Examiner*—Richard Raymond

[57] ABSTRACT

A process for the simultaneous production and purification of 4-nitro-o-phthalic anhydride which comprises subjecting an impure mixture containing 4-nitro-o-phthalic acid to azeotropic dehydration with selected azeotroping agents.

14 Claims, No Drawings

SIMULTANEOUS PRODUCTION AND PURIFICATION OF 4-NITRO-OMICRON-PHTHALIC ANHYDRIDE

BACKGROUND OF THE INVENTION

1. Field of the Invention

This invention relates to a process for the simultaneous production and purification of 4-nitro-o-phthalic anhydride from an impure mixture containing the same which comprises subjecting said impure mixture to azeotropic dehydration with selected azeotroping agents.

2. Description of the Prior Art

Converting pure 4-nitro-o-phthalic acid to 4-nitro-o-phthalic anhydride is not difficult. This can be done thermally for example, by merely heating the pure 4-nitro-o-phthalic acid at ambient pressure at a temperature of about 164° to about 165° C. for 3 to 4 hours. Water will be driven off and the desired pure anhydride will be obtained. Such conversion can also be effected chemically, for example by heating the pure 4-nitro-o-phthalic acid together with acetic anhydride under reflux. Water and acetic acid will be removed overhead, leaving behind desired anhydride. Acetic anhydride, however, is expensive, since it is consumed in the process. Moreover the use of such technique is not without some difficulty: after contact with excess acetic anhydride (reflux several hours), acetic anhydride is removed by atmospheric distillation and excess acetic anhydride is removed by relatively high vacuum (15 millimeters of mercury) distillation. Pot temperature may not exceed 120° C. or discoloration/charring of the product may result. The resulting product may then require post purification.

However, while such procedures can also be employed to convert 4-nitro-o-phthalic acid to the corresponding anhydride from an impure mixture containing said acid, the desired anhydride will still be present in admixture with the original impurities. In such cases, costly and difficult procedures would be necessary to obtain pure 4-nitro-o-phthalic acid, for the impurities would have to be removed from the impure mixture containing 4-nitro-o-phthalic acid prior to dehydration or from the anhydride mixture containing the impurity after dehydration.

SUMMARY OF THE INVENTION

We have found that we can obtain the simultaneous production and purification of 4-nitro-o-phthalic anhydride from an impure mixture containing the same by a process which comprises subjecting said impure mixture to azeotropic dehydration using as selected azeotroping agents specific aromatic compounds.

DESCRIPTION OF THE PROCESS

The impure mixture containing 4-nitro-o-phthalic acid sujected to thermal dehydration in accordance with the procedure defined and claimed herein can be any mixture known in the prior art which results in a mixture containing 4-nitro-o-phthalic acid and impurities associated therewith, for example, crude 4-nitro-o-phthalic acid that might be produced by the nitration of phthalimide and subsequent hydrolysis of 4-nitrophthalimide [Organic Synthesis, Collective Volume II, John Wiley and Sons, New York, 1943, pages 457 to 459].

An impure mixture that can especially be employed herein to obtain a purified 4-nitro-o-phthalic anhydride is that mixture resulting from the process defined and claimed in application Ser. No. 814,213, filed concurrently herewith, entitled Process for Preparing 4-Nitro-o-phthalic Acid. Briefly in the application indene, polyindene, dihydronaphthalene or polydihydronaphthalene is subjected to nitration in a first stage using aqueous nitric acid having a concentration of about 70 to 95 weight percent, preferably about 85 to about 95 weight percent, in a temperature range of about −40° to about 90° C., preferably about −10° to about 50° C., for about 1 minute to about 8 hours, preferably about 10 minutes to about 4 hours. In the second stage the nitrated compounds alone, after recovery from the nitration mixture, or the total nitrated product is then subjected to oxidation using aqueous nitric acid having a concentration of about 5 to about 50 weight percent, preferably about 10 to about 40 weight percent in a temperature range of about 135° to about 210° C., preferably about 155° to about 190° C., for about 0.1 to about 10 hours, preferably about 1 to about 4 hours. The product recovered, preferably used as charge herein, can have the following composition:

| Compound | Mol Per Cent Broad Range | Mol Per Cent General Range |
|---|---|---|
| 4-nitro-o-phthalic acid | 65–90 | 80–90 |
| 3-nitro-o-phthalic acid | 1– 6 | 2– 3 |
| phthalic acid | 0– 4 | 0.1– 1 |
| unidentified materials | 0–34 | 6–18 |

The 4-nitro-o-phthalic anhydride is obtained herein by subjecting an impure mixture containing the same to azeotropic dehydration in the presence of selected azeotroping agents. One of the azeotroping agents employed herein can be defined as follows:

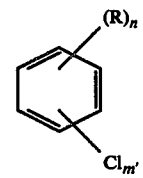

wherein R is an alkyl radical having from one to three carbon atoms, such as methyl, ethyl and propyl, n is an integer from 0 to 3, preferably 2, and m is an integer from 0 to 1, preferably 0. Specific examples of such compounds includes benzene, toluene, ethylbenzene, n-propylbenzene, isopropylbenzene (cumene), chlorobenzene, o-xylene, m-xylene, p-xylene, mixed xylenes, o-chlorotoluene, m-chlorotoluene, p-chlorotoluene, o-ethyltoluene, m-ethyltoluene, p-ethyltoluene, o-isopropyltoluene, m-isopropyltoluene, p-isopropyltoluene, o-diethylbenzene, p-diethylbenzene, etc. Preferred among these is ortho-xylene.

The system that is subjected to azeotropic dehydration herein will contain from about 1 to about 10 milliliters of the defined azeotropic agent per gram of the crude or impure 4-nitro-o-phthalic acid mixture, preferably from about 2 to about 6 milliliters of the azeotropic agent per gram of the crude or impure 4-nitro-o-phthalic mixture. Further purification of the desired product, for example, in removal of color bodies, can be effected, if desired, by having activated carbon present in the mixture being subjected to dehydration. When used, carbon can be present in an amount corresponding to about 0.01 to about 0.5 gram, preferably about 0.02 to about 0.25 gram, per gram of crude 4-nitro-o-phthalic acid mixture.

The total mixture, as defined above, is subjected to dehydration at a temperature of about 135° to about 190° C., preferably about 135° to about 160° C., and a pressure of about 100 millimeters of mercury to about 100 pounds per square inch gauge (about 0.14 to about 7.0 kilograms per square centimeter), preferably about ambient (atmospheric) pressure to about 50 pounds per square inch gauge (about 1.0 to about 3.5 kilograms per square centimeter), for a period of about 0.1 to about 10 hours, generally about 1 to about 8 hours.

Under the above conditions the 4-nitro-o-phthalic acid is converted to 4-nitro-o-phthalic anhydride and the resulting water and azeotroping agent are continuously removed overhead as an azeotrope. The azeotrope is cooled, for example, in the range of about 0° to about 100° C., preferably about 25° to about 50° C., resulting in the formation of two layers, an aqueous layer and a layer containing the azeotroping agent. The latter is continuously recycled to the reaction zone.

At the end of the dehydrating stage the material left behind will be the azeotroping agent, the desired 4-nitro-o-phthalic anhydride dissolved therein and other impurities, some soluble and some insoluble in the azeotroping agent. This mixture is then subjected to filtration at a temperature of about 50° to about 160° C., preferably about 70° to about 110° C., at any suitable pressure, for example ambient pressure. The resulting filtrate is then cooled to a temperature of about −10° to about 50° C., preferably about 0° to about 40° C., at any suitable pressure, for example, ambient pressure, as a result of which substantially pure 4-nitro-o-phthalic anhydride crystallizes out of solution. The latter can be recovered in any suitable manner, for example, by filtration. If desired, the 4-nitro-o-phthalic anhydride can be washed, for example, with a light hydrocarbon, such as hexane, to remove any occluded materials, such as azeotropic agent, associated therewith.

4-nitro-o-phthalic anhydride has many uses. For example, it can be reacted with KF to obtain 4-fluorophthalic anhydride suitable for the preparation of resins, for example, as in U.S. Pat. No. 3,956,321 to Markezich dated May 11, 1976.

DESCRIPTION OF PREFERRED EMBODIMENTS

Three runs were carried out wherein a crude 4-nitro-o-phthalic acid, containing about 75 to about 85 weight percent 4-nitro-o-phthalic acid, was converted to 4-nitro-o-phthalic anhydride of greater than 95 percent purity by azeotropic dehydration with o-xylene as the azeotroping agent.

Each of the crude 4-nitro-o-phthalic acid mixtures used were prepared in the following manner. Indene was added slowly, with stirring, to 90 percent aqueous nitric acid while maintaining a temperature in the range of about 8° to about 29° C., and the resulting solution was stirred at the selected temperature for 0.5 hour after completion of the indene addition. The product solution was poured onto a weighed amount of ice (200 grams) and the resulting mixture was diluted further with a measured amount of water (100 milliliters). Dilution of the concentrated acid solution with the ice and water caused nitroindenes (tan, granular solids) to precipitate. This mixture of aqueous acid and nitroindenes was charged to a 1-liter, stainless steel autoclave along with sufficient water (80 milliliters) to achieve a desired nitric acid concentration (25 percent). The autoclave was sealed, pressured with 50 pounds per square inch gauge (3.5 kilograms per square centimeter) of nitrogen and the mixture was heated with stirring to the desired oxidation temperature of about 174° to about 185° C. over a period of about 1 hour. Heating with stirring at the desired temperature was continued for an additional 1 to 2 hours. Maximum pressure during oxidation was controlled at a preset level of about 250 to about 255 pounds per square inch gauge (about 17.6 to about 17.9 kilograms per square centimeter) by an automatic pressure relief device. After cooling the system to ambient temperature over a period of 0.5 hour, pressure was released, the system flushed with nitrogen and the product mixture siphoned from the autoclave. The product mixture was vacuum filtered to separate a very small amount of suspended insoluble material and the clarified product solution was stripped by vacuum rotary evaporation. The resulting residue was thrice combined with fresh water (200 milliliters) and reevaporated to complete removal of excess nitric acid. The residue was found by gas chromatography to be largely 4-nitro-o-phthalic acid and was used in each of the first three runs herein. The 4-nitro-o-phthalic acid used in the fourth run was purchased from Eastman Kodak Co., Organic Chemicals Division (Catalog No. 3112).

Each of the crude mixtures defined above was combined with o-xylene and heated to reflux, with stirring, under a moisture test apparatus. After several hours of reflux, water ceased to be evolved, i.e., the amount of water collected in the overhead trap reached a constant level. The product was cooled to about 90° C. and vacuum filtered to separate a small amount of hot o-xylene insoluble impurities. Upon chilling (0°–5° C.) the clarified product solution, i.e., the filtrate, the desired product precipitated therefrom. The crystalline product was separated by vacuum filtration, washed with hexane to remove absorbed o-xylene and air dried to constant weight. Samples of the product were analyzed by gas chromatography as dilute acetone solutions using a six foot by ⅛-inch stainless steel column packed with 10 percent OV-1 on 80/100 Gas Chrom Q and operated isothermally at 175° C. A standard acetone solution of a mixture of 4-nitro-o-phthalic and 3-nitro-o-phthalic anhydrides was used as reference to determine composition of the product. The analysis indicated product contained greater than 95 percent of the desired 4-nitro-o-phthalic anhydride. The yield of isolated product was about 80 percent. In Run No. 3, activated carbon was incorporated in the dehydration system. After water removal was complete, the product mixture was cooled to about 90° C. and this hot product mixture was vacuum filtered through a bed of celite to remove both hot o-xylene-insoluble impurities and activated carbon. The color of the product isolated from this run was better (cream colored) than that from the other runs without activated carbon (light tan). An additional run was carried out following the procedure of Runs Nos. 1 to 4 wherein the charge employed was the same as in Runs Nos. 1 to 3 using o-chlorotoluene as the azeotroping agent at atmospheric pressure. The data obtained are summarized below in Table I.

TABLE I

| Run No. | Azeotroping Agent, Milliliters | Reflux[a] Time, Hours | Reflux[a] Temp. °C. | H₂O Off, Milliliters | Hot Insolubles,[b] Grams | Weight, Grams | Charge (C) and Product (P) GLC Assay, Mol Per Cent[c] 4NP | 3NP | P | O | Product, Melting point,° C. | Yield, Mol Cent[d] |
|---|---|---|---|---|---|---|---|---|---|---|---|---|
| 1 | o-xylene, 250 | 7.5 | 142–144 | 3.6 | 1.3 | C 50.0<br>P 28.9 | 76.8<br>95.6 | 3.6<br>1.4 | 1.6<br>0.04 | 18.0<br>3.0 | 105–113 | 82.3 |
| 2 | o-xylene, 230 | 5.0 | 142–144 | 4.0 | 1.1 not determined | C 50.6<br>P 30.2 | 82.9<br>98.6 | 2.5<br>1.2 | 0.5<br>0.01 | 14.1<br>0.2 | 108–114 | 78.7 |
| 3[e] | o-xylene, 225 | 7.1 | 142–144 | 4.2 |  | C 50.1<br>P 28.4[f] | 84.1<br>97.5 | 2.0<br>1.0 | 0.4<br>0.01 | 13.5<br>1.5 | 107–114 | 73.7 |
| 4 | o-xylene, 125 | 7.0 | 142–144 | 1.9 | 0.1 | C 25<br>P 20.1[f] | 98<br>>99 | —<br>— | —<br>— | 2.0<br><1 | 114–117 | 89.7 |
| 5 | o-chlorotoluene, 225 | 2.1 | 157–159 | 3.6 | 1.2 | C 50.8<br>P 31.0 | 82.7<br>95.3 | 2.1<br>1.2 | 0.5<br>0.05 | 14.7<br>3.4 | 106–113 | 80.7 |

[a]At atmospheric pressure
[b]Impurities removed by filtration of the hot product mixture
[c]In charge (c) 4NP = 4-nitro-o-phthalic acid; 3NP = 3-nitro-o-phthalic acid; P = phthalic acid; and O = other (unknowns). In product (P): 4NP = 4-nitro-o-phthalic anhydride; 3NP = 3-nitro-o-phthalic anhydride; P = phthalic anhydride; O = other (unknown)
[d]Product as 4-nitro-o-phthalic anhydride relative to 4-nitro-o-phthalic acid in charge
[e]3.8 grams of activated carbon added to dehydration system
[f]Cream-colored product; others light tan.

Three additional runs were carried out following the procedure of Runs Nos. 1 to 4 wherein the charge employed was the same as in Run No. 4 using other alkyl-aromatic azeotroping agents at atmospheric pressure.

Further three additional runs were carried out following the procedure defined above refluxing under slight nitrogen pressure using selected azeotroping agents. By operating under pressure, reflux occurred at a higher temperature and the evolution of water was completed in less time.

The data obtained from the latter six runs are summarized below in Table II.

TABLE II

| Run No. | Azeotroping Agent, Milliliters | Reflux Time, Hours | Reflux Temp. °C. | Pressure, Pounds Per Square Inch Gauge (Kilograms) Per Square Centimeter) | H₂O Off, Milliliters | Hot Insolubles,[a] Grams | Weight, Grams | Charge (C) and Product (P) GLC Assay, Mol Per Cent[b] 4NP | Other | Product Melting Point, °C. | Yield, Mol Per Cent[c] |
|---|---|---|---|---|---|---|---|---|---|---|---|
| 6 | mixed xylenes, 125 | 5.5 | 138–140 | ambient | 2.3 | 0.1 | C 25.0<br>P 11.8 | 98<br>>99 | 2<br>>1 | 117–119 | 52.7 |
| 7 | ethyl benzene, 125 | 6.0 | 134–136 | ambient | 2.3 | 0.1 | C 25.0<br>P 17.3 | 98<br>>99 | 2<br>>1 | 118–119 | 77.2 |
| 8 | cumene, 125 | 3.7 | 150–152 | ambient | 1.9 | not determined | C 25.0<br>P 18.6 | 98<br>>99 | 2<br>>1 | 117–119 | 83 |
| 9 | mixed xylenes, 125 | 3.6 | 146–152 | 2–3 (0.14–0.21) | 2.1 | 0.1 | C 25.0<br>P 17.0 | 98<br>>99 | 2<br>>1 | 116–118 | 75.9 |
| 10 | ethyl benzene, 125 | 4.0 | 147–154 | 3–5 (0.21–0.55) | 2.0 | 0.1 | C 25.0<br>P 18.8 | 98<br>>99 | 2<br>>1 | 116–119 | 83.9 |
| 11 | toluene 125 | 5.8 | 144–153 | 18–20 (1.26–1.41) | 2.1 | 0.1 | C 25.0<br>P 15.8 | 98<br>>99 | 2<br>>1 | 114–118 | 70.5 |

[a]Impurities removed by filtration of the hot product mixture
[b]In charge (c): 4NP = 4-nitro-o-phthalic acid; in product (P): 4NP = 4-nitro-o-phthalic anhydride
[c]Product as 4-nitro-o-phthalic anhydride relative to 4-nitro-o-phthalic acid in charge.

Obviously, many modifications and variations of the invention, as hereinabove set forth, can be made without departing from the spirit and scope thereof, and therefore only such limitations should be imposed as are indicated in the appended claims.

We claim:

1. A process for the simultaneous production and purification of 4-nitro-o-phthalic anhydride from an impure mixture, said impure mixture having been obtained by subjecting indene, polyindene, dihydronaphthalene or polydihydronaphthalene to nitration with aqueous nitric acid having a concentration of about 70 to about 95 weight percent in a temperature range of about −40° to about 90° C. for about 1 minute to about 8 hours and then subjecting the resulting nitrated product to oxidation with aqueous nitric acid having a concentration of about five to about 50 weight percent in a temperature range of about 135° to about 210° C. for about 0.1 to about 10 hours, which comprises subjecting said impure mixture to azeotropic dehydration in the presence of an azeotroping agent selected from the group consisting of an aromatic compound defined as follows:

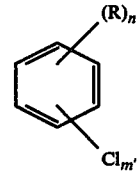

wherein R is an alkyl radical having from one to three carbon atoms, $n$ is an integer from 0 to 3 and $m$ is an integer from 0 to 1 by heating said impure mixture and said azeotroping agent at a temperature of about 135° to about 190° C. and a pressure of about 100 millimeters of mercury to about 100 pounds per square inch gauge for about 0.1 to about ten hours, thereby removing water and azeotroping agent, subjecting the resulting mixture containing azeotroping agent and 4-nitro-o-phthalic anhydride dissolved therein to filtration at a temperature of about 50° to about 160° C., cooling the resulting filtrate to a temperature of about −10° to about 50° C. to crystallize 4-nitro-o-phthalic anhydride therein and then recovering said crystallized 4-nitro-o-phthalic anhydride from said resulting filtrate.

2. The process of claim 1 wherein the alkyl radical is methyl and $n$ is the integer 2.

3. The process of claim 1 wherein the alkyl radical is methyl, $n$ is the integer 2 and $m$ is the integer 0.

4. The process of claim 1 wherein said aromatic compound is a xylene.

5. The process of claim 1 wherein said aromatic compound is o-xylene.

6. The process of claim 1 wherein said aromatic compound is ethyl benzene.

7. The process of claim 1 wherein said aromatic compound is cumene.

8. The process of claim 1 wherein said aromatic compound is toluene.

9. The process of claim 1 wherein said azeotropic dehydration is carried out at a temperature of about 135° to about 160° C. at a pressure of about ambient pressure to about 50 pounds per square inch gauge for about 1 to about 8 hours.

10. The process of claim 1 wherein the amount of azeotroping agent present is in the range of about 1 to about 10 milliliters per gram of said impure mixture.

11. The process of claim 1 wherein the amount of azeotroping agent present is in the range of about 2 to about 6 milliliters per gram of said impure mixture.

12. The process of claim 9 wherein at the end of said period the mixture is subjected to filtration at a temperature of about 70° to about 110° C. and the filtrate obtained is cooled to a temperature of about 0° to about 40° C. to crystallize 4-nitro-o-phthalic anhydride therein.

13. The process of claim 1 wherein the azeotrope containing water and said azeotroping agent removed from the dehydration zone is separated into its component parts and the recovered azeotroping agent is recycled to the dehydration zone.

14. The process of claim 12 wherein the azeotrope containing water and said azeotroping agent removed from the dehydration zone is separated into its component parts and the recovered azeotroping agent is recycled to the dehydration zone.

UNITED STATES PATENT OFFICE
CERTIFICATE OF CORRECTION

Patent No. 4,138,412                    Dated February 6, 1979

Inventor(s) John D. Bacha and Charles M. Selwitz

It is certified that error appears in the above-identified patent and that said Letters Patent are hereby corrected as shown below:

Title of Patent "SIMULTANEOUS PRODUCTION AND PURIFICATION OF 4-NITRO-OMICRON-PHTHALIC ANHYDRIDE"

should read    --SIMULTANEOUS PRODUCTION AND PURIFICATION OF 4-NITRO-o-PHTHALIC ANHYDRIDE--

Signed and Sealed this

First Day of May 1979

[SEAL]

Attest:

RUTH C. MASON
Attesting Officer

DONALD W. BANNER
Commissioner of Patents and Trademarks